US006171318B1

(12) United States Patent
Kugel et al.

(10) Patent No.: US 6,171,318 B1
(45) Date of Patent: *Jan. 9, 2001

(54) HERNIA MESH PATCH WITH STIFFENING LAYER

(75) Inventors: Robert D. Kugel, Olympia, WA (US); J. Douglas Inman, Arlington; Keith D. Biggers, Southlake, both of TX (US)

(73) Assignee: Bard ASDI Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/250,223

(22) Filed: Feb. 11, 1999

Related U.S. Application Data

(63) Continuation-in-part of application No. 09/006,653, filed on Jan. 14, 1998, now Pat. No. 5,916,225, which is a continuation of application No. 08/755,108, filed on Nov. 22, 1996, now Pat. No. 5,769,864, which is a continuation-in-part of application No. 08/315,249, filed on Sep. 29, 1994, now Pat. No. 5,634,931

(60) Provisional application No. 60/095,769, filed on Aug. 7, 1998.

(51) Int. Cl.[7] .................................................. A61B 17/04
(52) U.S. Cl. ................................ 606/151; 602/44; 602/58
(58) Field of Search ..................................... 606/151, 200, 606/213, 110, 113, 127; 623/1; 602/44, 58

(56) References Cited

U.S. PATENT DOCUMENTS

| | | | |
|---|---|---|---|
| 2,671,444 | 3/1954 | Pease, Jr. ........................... | 606/151 |
| 3,054,406 | 9/1962 | Usher ................................. | 606/151 |
| 4,007,743 | 2/1977 | Blake . | |
| 4,347,847 | 9/1982 | Usher ................................. | 606/151 |
| 4,452,245 | 6/1984 | Usher ................................. | 606/151 |

(List continued on next page.)

FOREIGN PATENT DOCUMENTS

WO 94/27535   12/1994   (WO) .

OTHER PUBLICATIONS

"Minimally Invasive, Non–Laparoscopic, Preperitoneal, Sutureless, Inguinal Hernorrhaphy" by Robert D. Kugel (not published). See Exhibit 2 of Declaration.

Gregory L. Brown, M.D. et al., "Comparison of Prosthetic Materials for Abdominal Wall Reconstruction in the Presence of Contamination and Infection", Annals of Surgery, Jun. 1985, vol. 201, pp. 705–711.

Scott D. Jenkins, M.D. et al., "A Comparison of Prosthetic Materials Used to Repair Abdominal Wall Defects", Surgery, Aug. 1983, vol. 94, No. 2, pp. 392–398.

(List continued on next page.)

Primary Examiner—Gary Jackson
(74) Attorney, Agent, or Firm—Wolf, Greenfield & Sacks, P.C.

(57) ABSTRACT

A hernia patch has a first layer of inert synthetic mesh material selectively sized and shaped to extend across and beyond a hernia. A second layer of inert synthetic mesh material overlies the first layer to create a generally planar configuration for the patch. The first and second layers are joined together by a seam that defines a periphery of a pouch between the layers. The pouch houses a stiffening layer to provide stiffness to the patch for urging the patch to conform to the generally planar configuration across the hernia as the surgeon withdraws his or her finger. An access slit is formed in one of the layers for insertion of a surgeon's finger or instrument into the pouch to allow the surgeon to facilitate insertion of the patch into the patient and to position the patch across the hernia.

10 Claims, 2 Drawing Sheets

U.S. PATENT DOCUMENTS

| | | | |
|---|---|---|---|
| 4,561,434 | 12/1985 | Taylor . | |
| 4,633,873 | 1/1987 | Dumican et al. | 606/151 |
| 4,655,221 | 4/1987 | Devereux | 606/151 |
| 4,693,720 | 9/1987 | Scharnberg et al. | 606/151 |
| 4,710,192 | 12/1987 | Liotta et al. . | |
| 4,769,038 | 9/1988 | Bendavid . | |
| 4,796,603 | 1/1989 | Dahlke . | |
| 4,854,316 | 8/1989 | Davis . | |
| 4,865,026 | 9/1989 | Barrett . | |
| 4,955,907 | 9/1990 | Ledergerber . | |
| 5,006,106 | 4/1991 | Angelchik . | |
| 5,059,205 | 10/1991 | El-Nounou et al. . | |
| 5,116,357 | 5/1992 | Eberbach | 606/151 |
| 5,122,155 | 6/1992 | Eberbach | 606/151 |
| 5,141,515 | 8/1992 | Eberbach | 606/151 |
| 5,147,374 | 9/1992 | Fernandez | 606/151 |
| 5,147,384 | 9/1992 | La Rocca . | |
| 5,147,387 | 9/1992 | Jansen . | |
| 5,176,692 | 1/1993 | Wilk et al. . | |
| 5,192,301 | 3/1993 | Kamiya et al. . | |
| 5,195,542 | 3/1993 | Gazielly et al. . | |
| 5,201,745 | 4/1993 | Tayot et al. . | |
| 5,254,133 | 10/1993 | Seid . | |
| 5,258,000 | 11/1993 | Gianturco . | |
| 5,290,217 | 3/1994 | Campos . | |
| 5,318,559 | 6/1994 | Mulhauser . | |
| 5,334,217 | 8/1994 | Das . | |
| 5,350,399 | 9/1994 | Erlebacher et al. | 606/151 |
| 5,356,432 | 10/1994 | Rutkow et al. . | |
| 5,366,460 | 11/1994 | Eberbach | 606/151 |
| 5,368,602 | 11/1994 | de la Torre | 606/151 |
| 5,370,650 | 12/1994 | Tovey et al. | 606/151 |
| 5,397,331 | 3/1995 | Himpens et al. . | |
| 5,425,744 | 6/1995 | Fagan et al. . | |
| 5,433,996 | 7/1995 | Kranzler et al. . | |
| 5,451,235 | 9/1995 | Lock et al. . | |
| 5,456,720 | 10/1995 | Schultz et al. . | |
| 5,507,811 | 4/1996 | Koike et al. . | |
| 5,593,441 | 1/1997 | Lichtenstein et al. . | |
| 5,614,284 | 3/1997 | Kranzler et al. . | |
| 5,695,525 | 12/1997 | Mulhauser et al. . | |
| 5,702,416 | 12/1997 | Kieturakis et al. . | |
| 5,716,408 | 2/1998 | Eldridge et al. . | |
| 5,743,917 | 4/1998 | Saxon . | |
| 5,766,246 | 6/1998 | Mulhauser et al. | 623/11 |
| 5,769,864 | 6/1998 | Kugel . | |
| 5,824,082 | 10/1998 | Brown . | |
| 5,836,961 | 11/1998 | Kieturakis et al. . | |
| 5,879,366 | 3/1999 | Shaw et al. | 606/151 |
| 5,916,225 | 6/1999 | Kugel . | |
| 5,919,232 | 7/1999 | Chaffringeon et al. | 606/151 |
| 5,922,026 | 7/1999 | Chin . | |
| 5,954,767 | 9/1999 | Pajotin et al. . | |

OTHER PUBLICATIONS

"Prevention of Postsurgical Adhesions by Interceed (TC7)", Fertility and Sterility, Jun. 1989, vol. 51, No. 6, pp. 933–938.

Hernando Cordona, M.D., "Prosthokeratoplasty", 1983, Cornea, vol. 2, No. 3, 1983, pp. 179–183.

Alonzo P. Walker, M.D., et al., "Double–Layer Prostheses for Repair of Abdominal Wall Defects in a Rabbit Model", pp. 32–37, Journal of Surgical Research, vol. 55, No. 1, Jul. 1993.

HERNIA MESH PATCH WITH STIFFENING LAYER

CROSS-REFERENCE TO RELATED APPLICATION

This application claims the benefit of provisional application Ser. No. 60/095,769, filed Aug. 7, 1998, and is a continuation-in-part of application Ser. No. 09/006,653, filed Jan. 14, 1998. U.S. Pat. No. 5,916,225, which was a continuation of application Ser. No. 08/755,108, Nov. 22, 1996, U.S. Pat. No. 5,769,864, which is a continuation-in-part of application Ser. No. 08/315,249, Sep. 29, 1994, U.S. Pat. No. 5,634,931.

TECHNICAL FIELD

The present invention generally relates to a surgically implantable patch for use in repairing a hernia of other wound. More particularly, the present invention relates to a hernia repair patch having a stiffening layer to maintain the patch in a planar configuration.

BACKGROUND

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. The repairs resulted in both a decrease in the recurrence rate as well as a decrease in the amount of a patient's post operative discomfort. Patients undergoing the more advanced procedures were able and are able to resume their normal activities sooner.

Some of the earlier techniques are somewhat complicated. Several use a plug or a locating member to fit within the hernia defect itself. Also, many of the earlier techniques were designed specifically for use in laparoscopic repair of hernias. Moreover, many of the prior inventions required suturing to the patient's body tissue. Although these medical advances are acknowledged for their usefulness and success, there remains a need or needs for more improvements in the surgical repair of hernias.

DISCLOSURE OF INVENTION

A hernia mesh patch for use in the surgical repair of a patient's inguinal, or other abdominal wall hernias, is disclosed for permanent placement within a patient's body space. The hernia mesh patch of the invention has a top layer and a bottom layer of an inert, synthetic mesh, preferably polypropylene mesh, secured to each other with a seam. The seam defines an interior pocket in the patch. One of the layers has a slit to provide access to the interior of the patch.

To provide stiffness for the patch, a stiffening layer having a circumference slightly smaller than the circumference of the seam is sealed into the patch to keep the hernia mesh patch expanded in a planar configuration. The stiffening layer is preferably made of a resilient mesh material similar to the top and bottom layer but having a greater stiffness. A border on at least one of the layers extends outward past the seam. The border preferably has slits to fill uneven voids in the patient's tissue and fit more tightly.

Without the need for general anesthesia, nor expensive laparoscopic instrumentation, a surgeon makes a small incision in the patient when repairing an inguinal hernia. The incision is approximately three centimeters long, and is arranged obliquely, approximately two to three centimeters above the internal ring location of the inguinal hernia.

Thereafter, the surgeon uses his or her fingers to readily fold and compact the hernia mesh patch and direct it through the incision and into the patient's preeritoneal space. The patch then unfolds and expands into a planar configuration due to the stiffening layer, thereby creating a trampoline effect. Using a finger inserted through an access slit in one of the layers of the patch, the surgeon moves the hernia mesh patch to cover the defect in the patient's abdominal cavity. Thereafter, the surgeon withdraws his or her finger and secures the incision with stitches.

Soon after surgery, the patient's body reacts to the mesh of the hernia mesh patch. In a short time the mesh becomes stuck, thereby keeping the hernia mesh patch in place. Thereafter, the patient's scar tissue grows into the mesh, typically between thirty and sixty days, to permanently fix the hernia mesh patch in its intended position over the repaired area.

Optionally, small holes are cut through both layers of the mesh inside the seam to increase friction and to minimize the sliding or migration of the hernia mesh patch after the patch is positioned. Additionally, small darts may be located on the patch to increase friction.

BEST MODE FOR CARRYING OUT THE INVENTION

Figure 1:
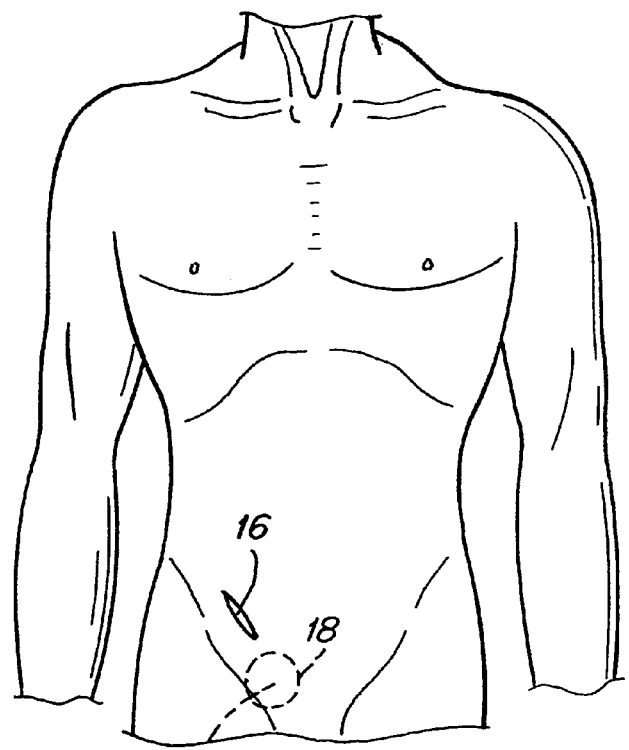
FIG. 1 is a schematic partial front view of a patient's body.

The hernia mesh patch 10, illustrated in the drawings, is surgically permanently implantable within a patient's body space to adequately cover, correct, prevent and repair any inguinal or other abdominal wall hernias or other types of hernias. The surgeon has the objective of making a sutureless repair, by first cutting an approximately three centimeter incision 16, which is obliquely positioned approximately two to three centimeters above the location described as the internal ring 18, where an inguinal hernia 14 has occurred, as shown in FIG. 1. The surgeon then works through incision 16 and inserts the hernia mesh patch 10.

Figure 2:
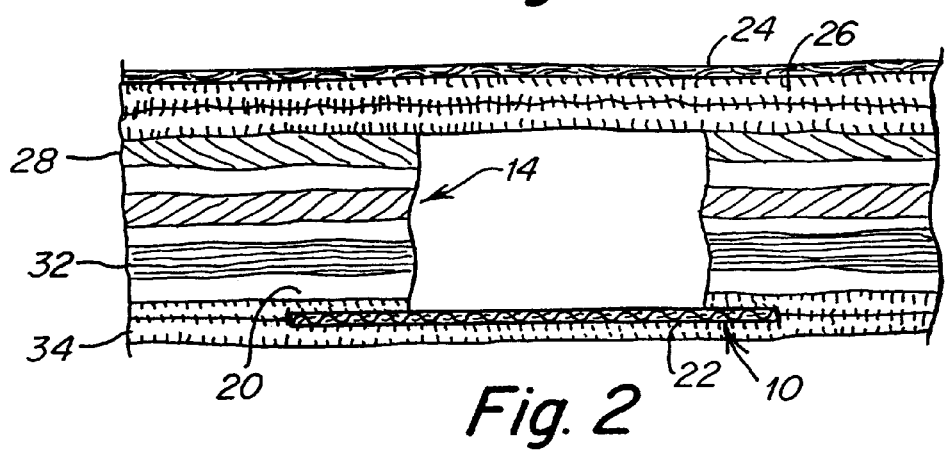
FIG. 2 is a schematic partial diagrammatic cross-section view of a patient's abdominal wall layers showing an inguinal or other abdominal wall hernia, where the surgically implantable hernia repair mesh patch has been correctly positioned in the preperitoneal created space.
Figure 6:
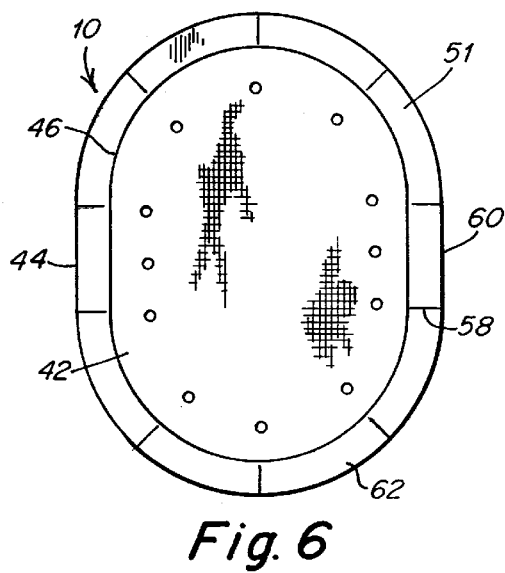
FIG. 6 is a top view of a preferred embodiment of the surgically implantable hernia repair mesh patch.

Hernia mesh patch 10 is illustrated in FIGS. 2 and 6. Hernia mesh patch 10 is particularly designed for the repair of an inguinal hernia 14, but may be used for other abdominal wall hernias or other tissue aperture repairs. The repair of an inguinal hernia is shown in FIG. 2. The surgeon dissects deeply into the patient's preperitoneal space 20, as indicated in FIG. 2, using a sharp instrument to make the incision 16 through the patient's skin 24, the subcutaneous fatty tissues 26, and the external oblique fascia 28, which has been cut parallel with its fibers a short distance. The surgeon then incises the transversalis fascia 32, creating an entrance into the preperitoneal space 20 above the peritoneum 34 at a location proximate to the hernia defect 14. In so doing, the surgeon identifies and frees up the hernia sac and creates the pocket 22 in the preperitoneal space 20. This space 20 underlies the area referred to as Hesselbach's triangle, in reference to both indirect and direct hernias. The surgeon's placement of the hernia mesh patch 10 in accordance with this method protects the entire inguinal floor, and therefore not only will the patch 10 repair or correct a single small hernia, but will also protect against future hernias through other potentially weakened areas.

Figure 3:
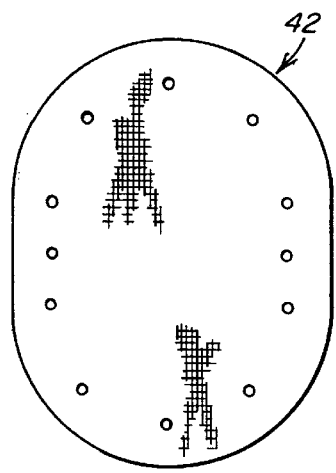
FIG. 3 is a top view of the bottom layer of the implantable hernia repair mesh patch of the invention.
Figure 4:
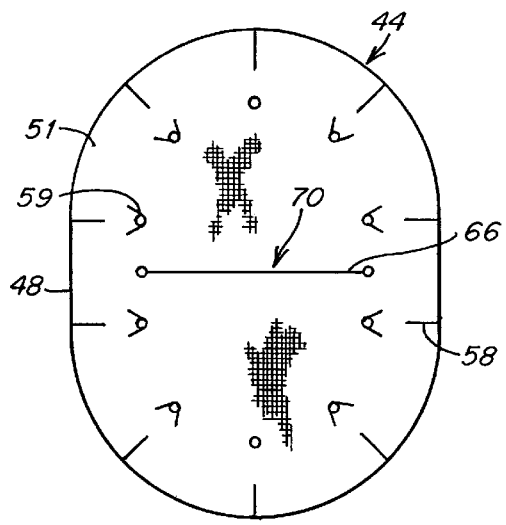
FIG. 4 is a top view of the top layer of the surgically implantable hernia repair mesh patch of the invention.

Hernia mesh patch 10 is composed of two similarly sized and shaped pieces, which are a bottom layer 42 (FIG. 3), and a top layer 44 (FIG. 4). Layers 42 and 44 are preferably made of an inert synthetic mesh material, such as polypropylene material. The mesh material is formed from monofilament material that is resistant to infection and that has been used safely in many hernia operations, in previous ways and in previous embodiments. Preferably, bottom layer 42 and top layer 44 of mesh material are made in a circle, loop, ovoid, or oval shape.

Figure 5:
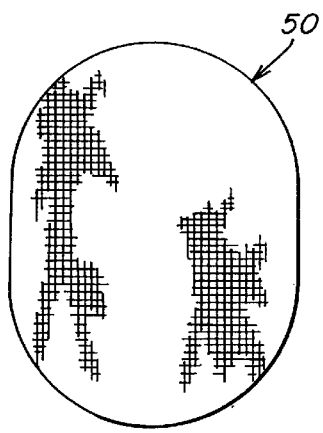
FIG. 5 is a top view of the stiffening layer of the invention.
Figure 7:
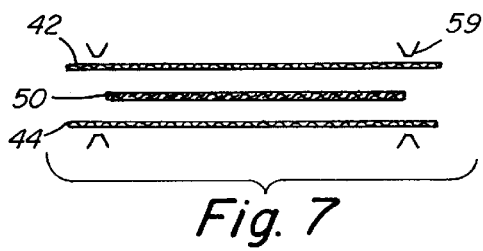
FIG. 7 is an exploded cross-sectional view of the patch of the invention.

Bottom layer 42 may be the same size as top layer 44 or a different size. A seam 46 (FIG. 6) joins the bottom layer 42 and top layer 44 together. The seam 46 is preferably created ultrasonically, although other techniques could be employed. In one embodiment, seam 46 is approximately one centimeter in from outer edge 48 of top layer 44 and bottom layer 42. The seam 46 surrounds a stiffening layer 50 (FIGS. 5 and 7) and holds layer 50 in place. Stiffening layer 50 is, therefore, encapsulated between bottom layer 42 and top layer 44 (FIG. 7).

Figure 8:
FIG. 8 is an enlarged view of a dart shown in FIGS. 4 and 7.

Stiffening layer 50 is a layer of mesh material that is resilient but has a greater stiffness than layer 42 or 44. Stiffening layer 50 may be made of polypropylene material similar to layer 42 and 44. Its greater stiffness may be as a result of using larger diameters of individual fibers, as compared to fibers in the bottom layer 42 or top layer 44 or its greater stiffness may result from other conventional techniques. The outer one centimeter of the mesh material of the layers 42, 44 is left free to serve as a border or apron 51 to fill uneven voids in the patient's tissue. The free border 51 serves to frictionally keep the patch 10 in its hernia repair position in a patient's preperitoneal space. Inside of the seam 46, like-size darts 59 (FIGS. 4, 7 and 8) may be positioned on either or both of the bottom mesh layer 42 and the top layer 44, preferably aligned one above the other. The presence of the darts 59 helps initially to frictionally keep the hernia mesh patch 10 in place. Thereafter, the patient's scar tissues grow in and around the darts 59 to continue to keep the hernia mesh patch in position. The outer one centimeter of top layer 44 may also be cut to form slits 58, which radially or diagonally create scalloped or fringed edges 60 that define tab portions 62 on top mesh layer 44.

The top layer 44 is cut to form slit 66 (FIG. 4) transversely at the center thereof, creating a finger access into an interior space or pouch 70. Pouch 70 is defined by the top and bottom layers 44, 42 of the synthetic mesh material and houses stiffening layer 50.

In use, at the conclusion of the surgeon's use of both sharp and blunt instruments to create a pocket in a patient's preperitoneal space, the surgeon selects the type and size embodiment of the hernia mesh patch 10 best suited to be used in the repair of the patient's defect or hernia 14. Hernia mesh patch 10 is folded and further compacted, as may be necessary, by the surgeon using his or her fingers, so that the selected patch 10 may be conveniently inserted through the wound or incision 16 and down into the patient's preperitoneal space. The hernia mesh patch 10 is then freed and allowed to expand. Thereafter, the surgeon uses his or her finger to manipulate patch 10 to continue any further expansion of patch 10 that may be necessary. The surgeon's finger may be inserted through the slit 66 in the top mesh layer 44 and the hernia mesh patch 10 may be positioned within the patient's preperitoneal space. The surgeon then withdraws his finger to complete the repair surgery by closing the wound or incision with stitches.

In the repair of other hernias, and especially those that are large, a direct incision is made. After placement of a large hernia mesh patch 10, the surgeon may use limited sutures to keep the larger hernia mesh patch 10 in place. Generally, the hernia mesh patch 10 of the invention may be positioned and left in place without the use of sutures.

The hernia mesh patch of the invention has many advantages. The hernia mesh patch is simple in design and method of insertion. The patch adequately underlies a hernia defect by a minimum of two centimeters around the circumference of the hernia defect, with sufficient rigidity and with sufficient friction to eliminate or minimize sliding or migration. When the hernia mesh patch is used, the repair of inguinal and other abdominal wall hernias are repaired through a small wound or incision, with less tension, less post-operative discomfort, shorter operating time, and at a potentially lower cost to the patient than traditional methods. The patient's post-operative discomfort is decreased, and risk of any recurrence is likewise decreased.

While the invention has been shown in one of its forms, it should be apparent that it is not limited to those embodiments but is susceptible to various changes without departing from the scope of the invention.

In the claims:

1. A tissue aperture repair patch for implanting within a patient, comprising:
   a first layer of inert synthetic mesh material sized and shaped to extend across and beyond a tissue aperture in a patient, the first layer having a planar configuration, being resilient and having a selected stiffness; and
   a resilient stiffening layer of inert synthetic material carried by and overlying the first layer for supporting the first layer in the planar configuration, the stiffening layer having a greater stiffness than the first layer.

2. The tissue aperture repair patch according to claim 1 further comprising a second layer joined to the first layer, said first layer and said second layer defining a pouch that encapsulates the stiffening layer.

3. A patch according to claim 2, further comprising:
   a slit in one of said first and said second layers for insertion of a finger into said pouch to position the patch across the tissue aperture.

4. The patch according to claim 1, wherein the first layer has an outer periphery that extends beyond the stiffening layer.

5. The patch according to claim 1, wherein a slit is in the first layer, and the first layer has an outer periphery that extends beyond the stiffening layer.

6. A tissue aperture repair patch for implanting in a patient, comprising:
   a first layer of inert synthetic mesh material sized and shaped to extend across and beyond a tissue aperture in a patient;

a second layer of inert synthetic mesh material secured to the first layer to create a pouch between the first and second layers;

an opening in the pouch for insertion of a finger into the pouch to position the patch across the tissue aperture; and a resilient stiffening layer within said pouch for supporting the first layer and the second layer, the stiffening layer being carried by the first layer and the second layer so as to remain implanted with the first layer and the second layer in the patient.

7. A patch according to claim 6, wherein the opening in said pouch comprises:

a slit in one of said first and said second layers.

8. The patch according to claim 6, wherein:

said first layer is secured to said second layer by a seam extending around a periphery of said pouch; and at least one of said first and said second layers has a border that extends beyond said seam to fill uneven voids in a patient's tissue.

9. The patch according to claim 6, wherein the support member is comprised of mesh monofilament fibers and has a greater stiffness than said first and said second layers.

10. A tissue aperture repair patch, comprising:

a first layer of inert synthetic mesh material sized and shaped to extend across and beyond a tissue aperture;

a second layer of inert synthetic mesh material overlying the first layer to create a generally planar configuration for the patch;

the first and second layers being joined together by a seam that defines a pouch between the layers;

an opening in one of the layers for insertion of a finger of a surgeon into the pouch to facilitate insertion of the patch into the patient and to position the patch across the tissue aperture; and a resilient stiffening layer of inert synthetic mesh material located within the pouch and proximate the seam for urging the patch to conform to the generally planar configuration across the tissue aperture as the surgeon withdraws his or her finger, the stiffening layer having a greater stiffness than said first and said second layers.

\* \* \* \* \*